United States Patent [19]

Chin et al.

[11] Patent Number: 5,190,551

[45] Date of Patent: Mar. 2, 1993

[54] CONTROLLED APPARATUS AND METHOD FOR EXTRACTING CEMENT MANTLES FROM BONE RECESSES

[75] Inventors: Albert K. Chin, Palo Alto; Milton B. McColl, Los Altos; Kathryn J. Hoffman, Redwood City; Diane E. Caramore, San Francisco, all of Calif.

[73] Assignee: Zimmer, Inc., Warsaw, Ind.

[21] Appl. No.: 628,390

[22] Filed: Dec. 14, 1990

[51] Int. Cl.⁵ .............................................. A61B 17/56
[52] U.S. Cl. ..................................... 606/99; 606/100; 606/86
[58] Field of Search .................. 606/53, 60, 72, 73, 606/79, 86, 92, 93, 94, 96, 100, 104

[56] References Cited

U.S. PATENT DOCUMENTS

| | | |
|---|---|---|
| 824,983 | 7/1906 | Farrington . |
| 2,243,717 | 5/1941 | Moreira ................................ 128/92 |
| 3,334,624 | 8/1967 | Schneider et al. .................... 128/92 |
| 3,585,994 | 6/1971 | Huggler ........................... 606/100 X |
| 3,915,162 | 10/1975 | Miller ................................ 128/92 |
| 4,175,555 | 11/1979 | Herbert ............................ 128/92 B |
| 4,222,382 | 9/1980 | Antonsson et al. .................. 128/92 |
| 4,248,232 | 2/1981 | Engelbrecht et al. .............. 128/305 |
| 4,399,813 | 8/1983 | Barber ............................ 606/100 X |
| 4,463,753 | 8/1984 | Gustilo ............................. 128/92 B |
| 4,476,861 | 10/1984 | Dimakos et al. ................. 128/303 R |
| 4,546,767 | 10/1985 | Smith ................................. 606/93 |
| 4,612,922 | 9/1986 | Barber ............................. 128/92 R |
| 4,616,638 | 10/1986 | Griggs ............................ 128/92 BB |
| 4,686,971 | 8/1987 | Harris et al. .................... 128/92 VT |
| 4,702,236 | 10/1987 | Tarabichy et al. ............... 128/92 V |
| 4,834,081 | 5/1989 | Van Zile ......................... 128/92 VT |
| 4,838,264 | 6/1989 | Bremer et al. .................. 128/303 B |
| 4,846,161 | 7/1989 | Roger .............................. 128/92 V |
| 4,858,601 | 8/1989 | Glisson ............................ 128/92 R |
| 4,919,153 | 4/1990 | Chin .................................. 606/93 |
| 5,041,120 | 8/1991 | McColl et al. ................... 606/92 X |
| 5,047,035 | 9/1991 | Mikhail et al. ..................... 606/93 |

FOREIGN PATENT DOCUMENTS 312857A  4/1989  European Pat. Off. .

OTHER PUBLICATIONS

*Techniques in Orthopedics*, "Revision of Total Hip and Knee", Lawrence D. Dorr, M. D., pp. 14–22.
"Revision in Surgery for Failed, Monseptic Total Hip Arthroplasty-The Femoral Side", William H. Harris, M.D., pp. 8–20.
*The Micro-Aire Cement Removal System*, Micro-Aire Surgical Instruments, Inc.
*Moglichkeiten der Anwendung von Ultraschallwerkzeug bei Endoprothesenwechsel*, E. Nieder, E. Engelbrecht, U. Röder und E. Strickle, Der Chirurg, 1979.

Primary Examiner—Robert A. Hafer
Assistant Examiner—Sam Rimell
Attorney, Agent, or Firm—Todd A. Dawson

[57] ABSTRACT

A cement plug received within a bone recess is extracted by forming a bore within the plug, tapping the bore to form internal screw threads therein, engaging the threads with a pulling tool, and applying tension to the tool to extract the plug. The bore is formed through means of a rod inserted into the plug while in a fluid state and/or a drill bit having a tubular guide received therearound to maintain the bit in generally aligned condition with the bone recess and limit the depth to which the bit penetrates the plug. The degree to which the bore is tapped and engaged by the pulling tool is controlled to avoid exceeding the extent of the bore and the screw threads formed therein. One embodiment employs a self-tapping extraction rod which serves both as a tap to form the screw threads and as the pulling tool to apply tension to extract the plug. Another embodiment employs a tap which is separate from the pulling tool. In both embodiments, a sleeve received around the tap and tool serves to measure and limit the extent to which the screw threads are formed and engaged.

2 Claims, 4 Drawing Sheets

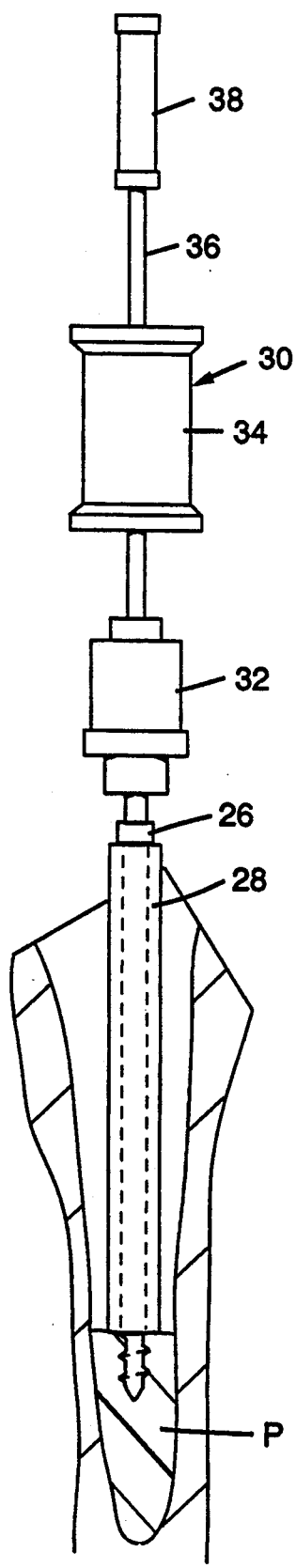
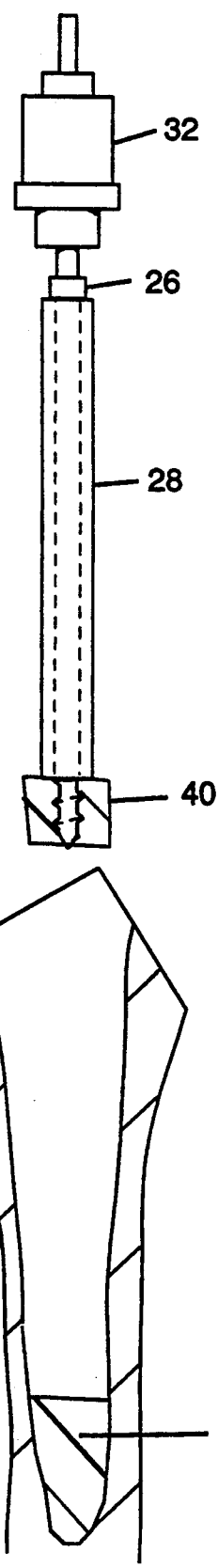
FIG. 7  FIG. 8

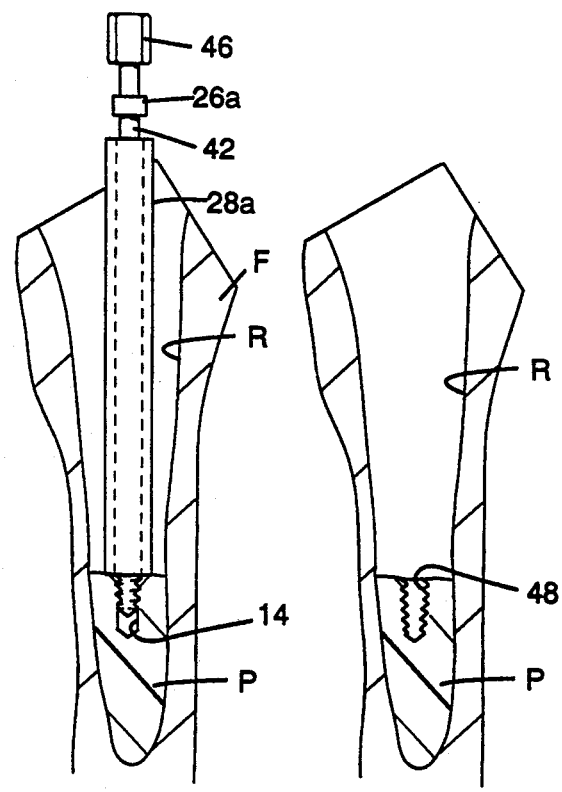
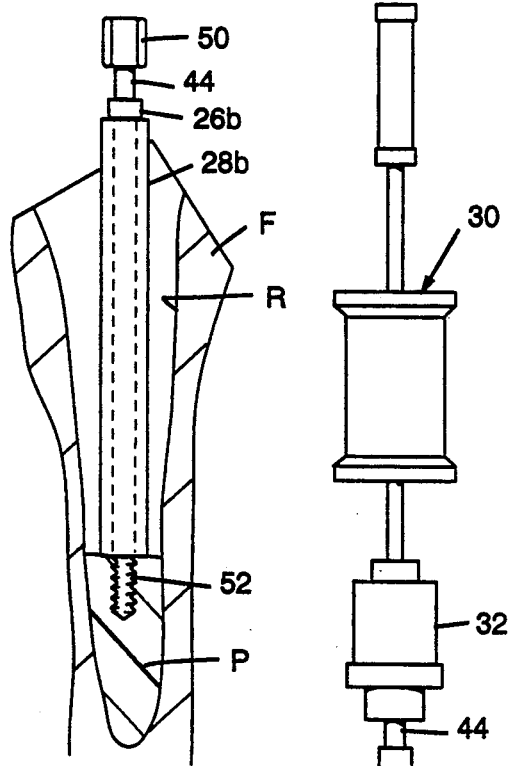
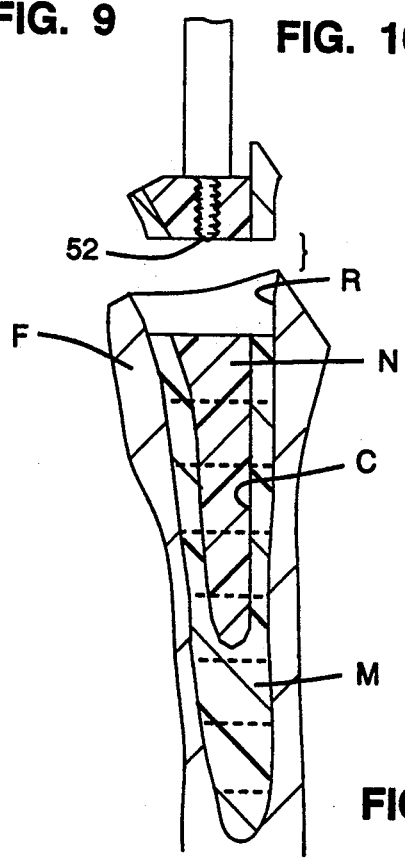
FIG. 9  FIG. 10  FIG. 11  FIG. 12  FIG. 13

CONTROLLED APPARATUS AND METHOD FOR EXTRACTING CEMENT MANTLES FROM BONE RECESSES

BACKGROUND OF THE INVENTION

The present invention relates to an improved method and apparatus for extracting the cement mantles used to secure prosthetic appliances, such as joint components, in bone recesses. In its more specific aspects, the invention is concerned with the removal of distally located cement plugs which are not readily removable by the invention of U.S. Pat. No. 4,919,153 by Albert K. Chin.

The invention of U.S. Pat. No. 4,919,153 achieves removal of an old cement mantle during revision arthroplasty by injecting new cement into the appliance cavity within the mantle left by removal of a prosthetic appliance, and then embedding a pulling tool within the cement. The new cement and old mantle bond into a unitary mass and then the pulling tool is used to remove the mass from the bone recess, as a unit.

In practice, it has been found that a solid plug of cement is often present distal to the tip of the cavity left by the removed prosthetic appliance. U.S. patent application Ser. No. 467,742, now U.S. Pat. No. 5,041,120 filed Jan. 19, 1990, a continuation-in-part of the application for U.S. Pat. No. 4,919,153, is concerned with a technique for removing this plug wherein the plug is drilled before the addition of new cement and the placement of the pulling tool. This allows the pulling tool to bond along most of the entire length of the cement mantle.

In many cases of cement extraction, it is impossible to pre-drill the plug, as provided by application U.S. Pat. No. 5,041,120 due to deviated alignment of the cavity within the mantle. Any attempt to drill such a plug will result in perforation of the femur. In these situations, the proximal portion of the cement mantle may be successfully extracted through the technique of U.S. Pat. No. 4,919,153, leaving a solid distal plug.

Prior art tap extraction systems for the removal of solid cement plugs employ a drill to first drill a bore into the plug and then a tap which, together with a slaphammer secured thereto, serves as a pulling tool to remove the plug. Unfortunately, these systems function poorly in the majority of cases. The solid plug is generally tightly held in the bone and available tap extractors strip out without removing the cement plug. In other cases, the tap extractor cracks the cement plug during extractor placement. Femoral perforation also occurs during drilling of the plug in preparation for tap placement. Strippage of the tap extractor occurs because the fluted configuration of the tap provides insufficient thread strength for plug removal. Plug drilling is difficult to perform without femoral perforation because of the long stem of the drill required to drill deep into the plug and the hardness and irregularity of the surface of the plug. The drill often glances off and punctures through the bone. After the plug is drilled, the tap is advanced through the drilled bore and often advanced too far, with resultant strippage of the cement threads. Radial forces exerted by the tap during tap placement also lead to cracking of the cement plug.

SUMMARY OF THE INVENTION

The present invention provides for the controlled drilling, tapping and removal of the distal plug of cement often present in a bone recess after removal of a prosthetic appliance. It may also be used to incrementally remove all or part of an elongate cement mantle after the mantle has been filled with new cement and the cement has been permitted to harden into a bonded unitary mass with the mantle.

The basic components of the apparatus comprise a drill bit and guide to form a limited depth bore within a plug located at the distal end of a bone recess and a tap to form a screw thread within the bore. An indicating or measuring sleeve is receivable around the tap to enable penetration of the tap into the bore to be limited to no more than the depth of the bore. The tap may take the form of a self-tapping screw which also serves, together with a slaphammer secured thereto, as the tool to remove the plug from the recess. Alternatively, the tap may take the form of a machine tap which is removed after it performs its tapping function and followed by a separate threaded pulling tool which, together with a slaphammer secured thereto, is used to remove the plug. When a machine screw type pulling tool is used, an indicating or measuring sleeve is received around the tool during its placement to assure that engagement of the tool with the threaded bore is limited to no more than the depth of the bore.

The present invention may be used to remove the entirety of a cement mantle by first injecting new cement to the cavity of the mantle and permitting the new cement and mantle to bond into an integral mass. The steps of forming a limited depth bore, threading the bore, and imparting pulling force to the bore through means of a pulling tool are then successively repeated to remove the entire mantle, in segments. When used for this purpose, the kit may also include a volume of fluid cement to fill the cavity and a smooth elongate rod to form a bore in the injected cement. The rod may be curved to conform to the shape of the cavity.

A principal object of the present invention is to provide an improved method and apparatus for removing a cement plug located in the distal end of an elongate bone recess.

Another object of the invention is to provide such a method and apparatus which enables the plug to be drilled and tapped for removal, with a minimum of risk that the drill will result in bone perforation, or that the tap will fracture the plug prior to removal.

Still a further object related to the latter object is to provide such a method and apparatus wherein engagement of the pulling tool with the plug may be controlled to minimize the risk that the tool will strip the threads formed within the plug.

Still another object of the invention is to provide such a method and apparatus which is ideally suited for use with a cement extraction system of the type disclosed in U.S. Pat. No. 4,919,153 wherein a mantle of polymethyl methacrylate (PMMA) is removed by first pulling the prosthetic appliance from the mantle and then filling the cavity left by the mantle with newly mixed PMMA.

Another general object of the invention is to provide such a method and apparatus wherein radial forces exerted on the plug and the bone within which the plug is received are minimized.

Still another and more specific object of the invention is to provide such a method and apparatus wherein a drill guide serves to enable drilling of a limited depth bore in a plug at the distal end of an elongate bone recess, without risk that the drill will deviate from centered condition relative to the plug.

Another specific object of the invention is to provide a method and apparatus for tapping a limited depth bore in a plug disposed at the end of an elongate recess, without concern that the tap will penetrate beyond the depth of the bore and thus strip the threads.

A further object of the invention is to provide a method and apparatus for forming a curvilinear bore in a new mass of cement injected into a deviated cavity of a cement mantle.

These and other objects will become more apparent when viewed in light of the following detailed description and accompanying drawings.

BRIEF DESCRIPTION OF THE DRAWINGS

FIG. 7 is a cross-sectional elevational view corresponding to FIG. 6, illustrating a slaphammer secured to the self-tapping screw and conditioned for use in removing a segment of the plug;

FIG. 8 is a cross-sectional elevational view corresponding to FIG. 7, illustrating the screw after it has been subject to impact by the slaphammer to remove a segment of the plug from the recess within the femur;

FIG. 9 is a cross-sectional elevational view similar to FIG. 5, illustrating a second embodiment of the invention wherein a machine screw tap is being used to form threads within the bore of a plug of cement received within the femur;

FIG. 10 is a cross-sectional elevational view corresponding to FIG. 9, illustrating the plug after the tap of FIG. 9 has been removed therefrom;

FIG. 11 is a cross-sectional elevational view corresponding to FIG. 10, illustrating a machine screw pulling tool threadably engaged with the machine threads formed by the tap of FIG. 9, with an indicator sleeve received around the tool to limit the degree of penetration of the pulling tool into the bore;

FIG. 12 is a cross-sectional elevational view corresponding to FIG. 11, illustrating a slaphammer secured to the pulling tool;

FIG. 13 is a cross-sectional elevational view illustrating a femur having a cement mantle received therein which needs to be removed as part of revision hip arthroplasty, showing a first alternative extraction system wherein the present invention is used with the injection of new cement into the mantle to progressively remove the entire mantle;

DESCRIPTION OF THE FIRST EMBODIMENT

Figure 1:
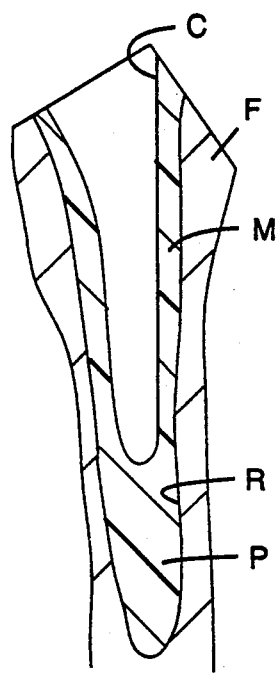
FIG. 1 is a cross-sectional elevational view, with parts thereof broken away, illustrating a femur having a cement mantle received therein which needs to be removed as part of revision hip arthroplasty.

FIG. 1 shows a femur "F" having a recess "R" formed therein and a polymethyl methacrylate cement mantle "M" within the recess. As there shown, a cavity "C" has been left within the mantle as a result of the removal of a prosthetic hip joint appliance therefrom. FIG. 1 also shows a solid plug of cement "P" forming part of the mantle "M" and positioned in adhered condition within the distal end of the recess "R".

Figure 2:
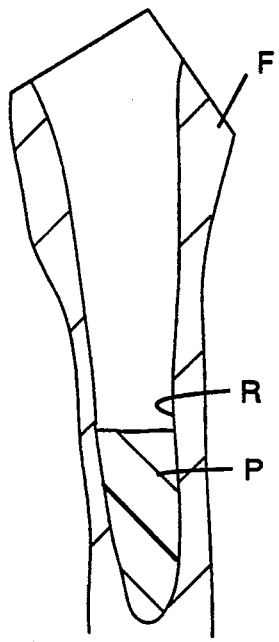
FIG. 2 is a cross-sectional elevational view similar to FIG. 1, illustrating the femur after the upper portion of the mantle has been removed, with a solid plug of the cement mantle left in place at the distal end of the recess within the femur.

FIG. 2 shows the femur of FIG. 1, after the proximal portion of the mantle "M" has been removed, as for example by the process of U.S. Pat. No. 4,919,153. As there shown, the plug "P" is left in place within the distal end of the recess "R".

Figure 3:
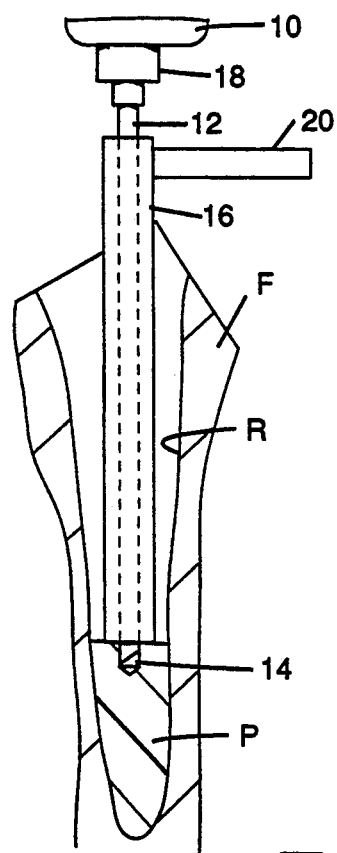
FIG. 3 is a cross-sectional elevational view corresponding to FIG. 2, illustrating a drill being used to form a bore within the plug through means of the drill guide of the present invention.

The first step for removing the plug "P" through means of the first embodiment is illustrated in FIG. 3. As there shown, a drill 10 having a bit 12 engaged in its chuck is in the process of drilling a bore 14 within the plug. A tubular drill guide 16 is received around the bit 12 for engagement with the plug "P" at its lower end and with the drill chuck, designated 18, at its upper end. Guide 16 is of a diameter sufficient to permit the bit 12 to freely rotate and axially slide within the guide. A handle 20 is fixed to and extends laterally from the upper end of the guide.

In use, the guide 16 maintains the bit in longitudinal alignment with the plug "P" and prevents the bit from deviating laterally into engagement with the bone of the femur "F". The guide 16 also limits the degree to which the bit can penetrate the plug "P". In the preferred embodiment, this penetration is limited to a depth of one inch and the bore formed by the drill has a diameter of 3/16 inch.

Figure 4:
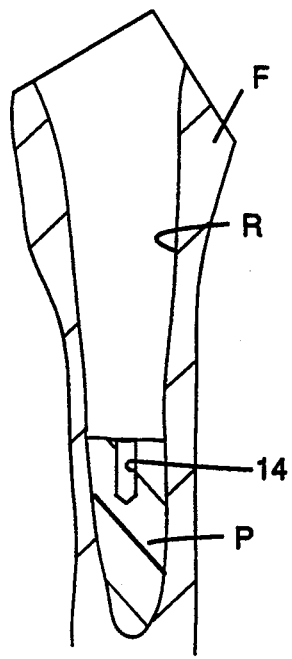
FIG. 4 is a cross-sectional elevational view corresponding to FIG. 3, illustrating the plug after the bore has been formed therein and the drill has been removed.
Figure 5:
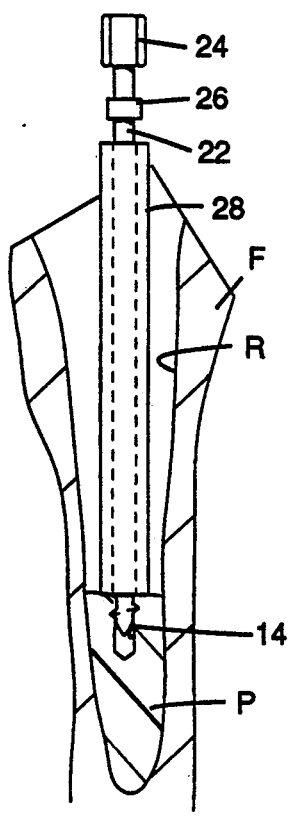
FIG. 5 is a cross-sectional elevational view corresponding to FIG. 4, illustrating a self-tapping screw being threaded into the bore within the plug, with an indicator sleeve received around the screw to limit penetration of the screw into the bore.

FIG. 4 shows the femur after the bore 14 has been formed to its full depth within the plug "P" and the drill bit 12 and guide 16 have been removed. Once so conditioned, a self-tapping extraction rod 22 is screwed into place within the bore as shown in FIG. 5. The rod consists of a distal screw threaded section ¾ inches in length. The screw thread is of a uniform outer diameter, and tapered only at its most distal portion for pilot purposes. This uniform diameter decreases the radial forces exerted on the brittle cement of the plug that tend to promote cement cracking, in contrast to screw forms that are tapered along their entire length.

Figure 6:
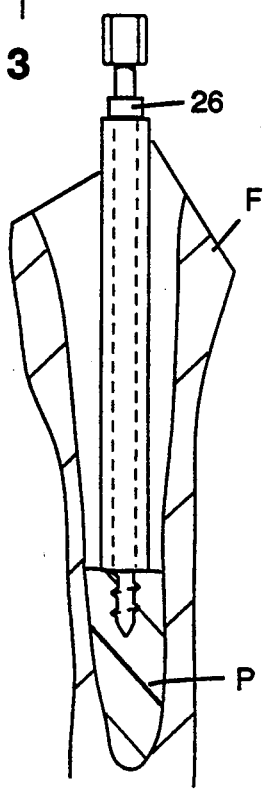
FIG. 6 is a cross-sectional elevational view corresponding to FIG. 5, illustrating the self-tapping screw after it is screwed fully into place to the extent permitted by the indicator sleeve.

The rod 22 is elongate and formed with a hexagonal head 24 at its upper end. An indicator collar 26 is fixed to the rod below the head 24. An indicator sleeve or tube 28 is slidably received on the rod beneath the collar 26. The lower end of the sleeve 28 engages the top surface of the plug "P" and the sleeve is of such a length as to engage the collar 26 when the rod is advanced sufficiently to engage the screw threaded end thereof with the full length of the bore 14, but no more than that length. Thus, the sleeve 28 and indicator collar 26 prevent the self-tapping extraction rod from over advancement and strippage from the cement plug, or cracking of the plug. The fully engaged condition of the rod, with the collar 26 and sleeve 28 contacting to indicate maximum penetration of the rod into the bore 14, is shown in FIG. 6.

FIG. 7 shows the extraction rod coupled to a slap hammer 30 by a quick disconnect coupler 32. Both the slaphammer and coupler are of conventional construction. In the preferred embodiment, the slap hammer has a 5 lb. weight 34 which is slidable along a rod 36 coupled to the extraction rod 22 by the coupler 32. In use, the weight is slid along the rod 36 to impact a stop 38 and impart tension to the extraction rod 22.

FIG. 8 shows the FIG. 7 assembly, after the extraction rod has broken away an approximately ¾ inch long segment 40 of the plug "P". At this stage, the segment 40 would be removed from the extraction rod 22 and the steps of FIGS. 3 to 8 would be successively repeated until the entire plug "P" was fully removed from the recess "R".

Description of the Second Embodiment

This embodiment is illustrated in FIGS. 9 to 12 and differs from the first embodiment in that, rather than using a self-tapping screw which serves as the extraction rod, it uses a machine tap 42 to form machine screw threads in the bore 14 and a separate extraction rod 44 which is engaged with the machine screw threads formed by the tap after the tap is removed. The advantage of this system, with separate tap and extraction rod as opposed to a self-tapping extraction rod, is a decreased incidence of cement cracking during thread formation. The flutes of the machine tap allow the cement particles formed during thread cutting to be displaced proximally, further reducing radial forces exerted against the brittle cement plug. With the self-tapping extraction rod of the first embodiment, the rod must still displace cement during the threading process, resulting in a greater amount of radial force against the sides of the drilled hole in the cement plug.

FIG. 9 shows the machine tap 42 in the process of forming machine screw threads in the bore 14. As there shown, an indicator sleeve or tube 28a, corresponding to the sleeve 28, is slidably received on the tap 42 and a collar 26a is fixed to the tap. The collar 26a and sleeve 28a function in a manner identical to the corresponding elements of the first embodiment to limit the degree to which the tap can penetrate the bore so that a tap does not exceed the length of the bore. The upper end of the tap 42 is provided with a hexagonal head 46 to enable it to be turned into and out of place.

FIG. 10 shows the plug "P" after the tap 42 has been removed, with the bore 14 having machine screw threads 48 formed over its length.

In FIG. 11, the machine screw threads 48 have been engaged by the threads of the extraction rod 44. The rod 44 is provided with a hexagonal head 50 to enable it to be turned into and out of place. A collar 26b is fixed to the rod 44 and an indicator sleeve or tube 28b is slidably received on the rod 44 beneath the collar 26b. The collar 26b and sleeve 28b function in a manner corresponding to the elements 26 and 28 of the first embodiment to limit the degree to which the rod 44 is threaded into the bore 14 so that penetration of the rod does not exceed the length of the bore.

FIG. 12 shows the second embodiment with a slaphammer 30 connected to the extraction rod 44 by a coupler 32. As there shown, the threaded end of the rod 44, designated 52, is fully engaged in the threads 48 of the bore 14. The operation of the slaphammer shown in FIG. 12 is identical to that described with reference to FIGS. 7 and 8. Accordingly, it will be appreciated that the rod 44 would remove a segment of the plug "P" corresponding in length to that of the bore 14. Where the plug has a length greater than that of the bore, this would leave a distal end portion of the plug in place within the recess "R". The steps of FIGS. 9 to 12 would be repeated until the plug was removed in its entirety.

Description of the First Alternate Extraction System

FIG. 13 shows an alternate extraction system wherein the present invention is used to remove the entire length of a cement mantle "M". In this embodiment, the stem of the prosthetic appliance would be removed in the usual manner and the cavity in the mantle would be cleaned, after which a new mass of cement "N" is injected into the cavity and permitted to cure to a hardened state. Where the mantle is PMMA, the new mass of cement would be of the same composition. Such cement has the quality that it serves to soften the cement of the old mantle and, upon curing, become a hardened integral part thereof.

Once the new mass of cement has cured and fully hardened within the mantle "M", it is successively removed in segments as depicted by the dashed transverse lines shown in FIG. 13. Where the first embodiment process is used, each segment would be removed by a series of steps corresponding to those depicted in FIGS. 3 to 8. Where the second embodiment system is used, each segment would be removed by a series of steps corresponding to those depicted in FIGS. 9 to 12.

Description of the Second Alternate Extraction System

Figure 14:
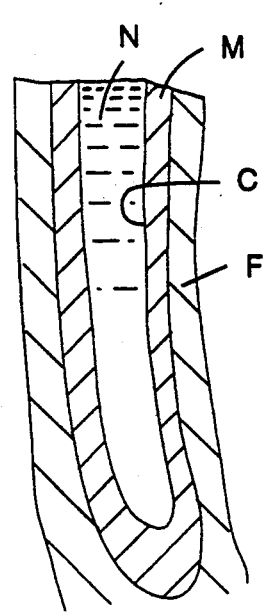
FIG. 14 is a cross-sectional elevational view illustrating a femur having a cement mantle received therein which needs to be removed as part of revision arthroplasty, showing fluid cement injected into the cavity within the mantle as the first step of a second alternative extraction system wherein the present invention is used to progressively remove the entire mantle.

FIGS. 14 to 20 show another alternate extraction system wherein the present invention is used to remove the entire length of a cement mantle "M". As shown in these figures, the cavity "C" in the mantle is deviated, as contrasted to being relatively straight. FIG. 14 shows the mantle after the prosthetic appliance has been removed to leave the deviated cavity and the cavity has been cleaned and filled with a new mass of cement "N".

As there shown, the new mass of cement "N" is still in a fluid state.

Figure 15:
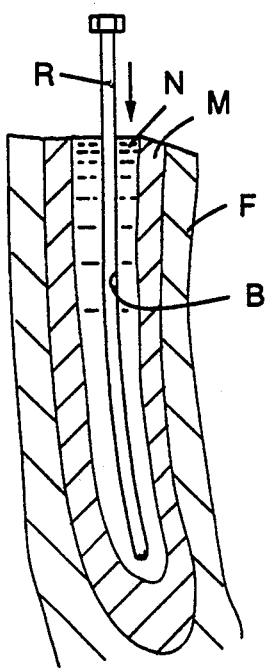
FIG. 15 is a cross-sectional elevational view similar to FIG. 14, showing a smooth elongate rod inserted into the fluid cement in the cavity of the mantle to form a bore therein as the second step of the second alternative extraction system.

FIG. 15 shows the second step of the second alternative embodiment wherein a rod "R" bent to conform to the shape of the deviated cavity is inserted into the new mass of cement "N" to form a bore "B" through the full length of the fluid mass of cement "N". The rod "R" is left in place until the new mass of cement "N" has cured and hardened.

Figure 16:
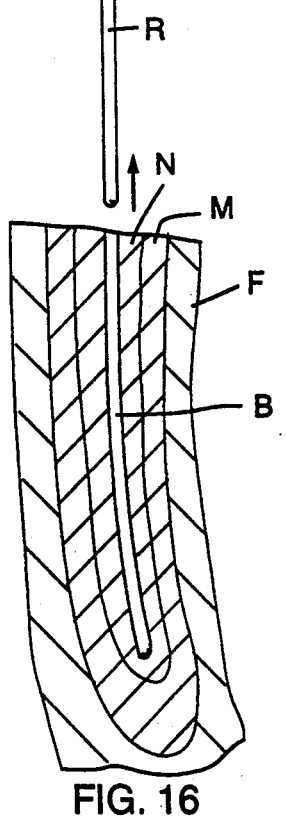
FIG. 16 is a cross-sectional elevational view similar to FIG. 15, showing the elongate rod being removed from the cement in the cavity after the cement has cured.

FIG. 16 shows the third step of the second alternative embodiment wherein the rod "R" is removed from the new mass of cement "N" to leave a smooth bore "B" therein. In the preferred embodiment, the rod is formed or coated with an external surface having a low coefficient of friction to facilitate such removal.

Figure 17:
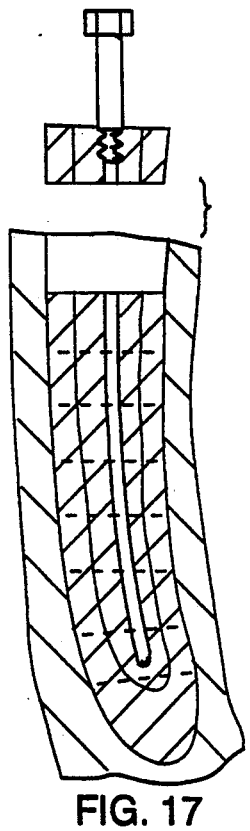
FIG. 17 is a cross-sectional elevational view similar to FIG. 16, illustrating a self-threading pulling tool engaged with the bore formed by removal of the elongate rod, with dashed lines extending across the mantle to illustrate how the second alternative embodiment is used to progressively remove the mantle.

FIG. 17 illustrates the fourth step of the second alternative embodiment wherein the mantle "M" is removed in segments, as depicted by the transverse lines shown in that figure. In this process, each successive segment is engaged with an extraction rod threaded into the bore "B". The extraction rod may either be of the self-threading type 22, or of the machine screw type 44. The use of the rods differs from that of the first and second embodiments only in that it is not necessary to drill a bore for receipt of the rod, since such a bore has already been provided by the rod "R".

Figure 18:
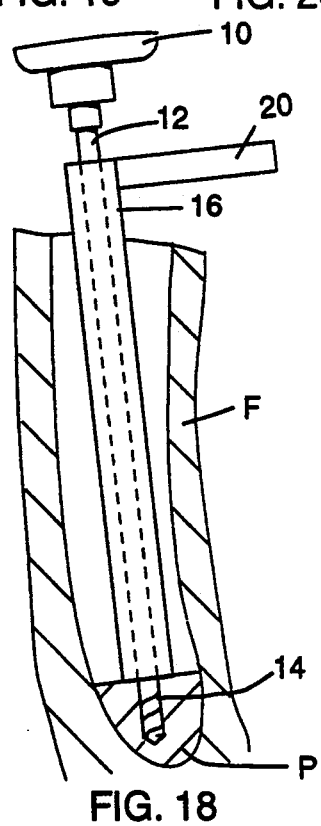
FIG. 18 is a cross-sectional elevational view similar to FIG. 17, illustrating a drill being used to form a bore within a solid plug of cement left in place in the distal end of the recess within the femur.

At the end of the removal of the length of cement through which the bore "B" extends, a plug "P" remains in the recess "R", as depicted in FIG. 18. As there shown, the plug is being drilled in a manner corresponding to that shown in FIG. 3 to form a bore 14 therein. Once so conditioned, the plug may be removed by steps corresponding to those of FIGS. 5 to 8, or 9 to 12.

The second alternative extraction system has the advantage that it is not necessary to drill the bore within the new mass of cement injected into the cement mantle. Rather, an elongate bore is formed by the rod "R". It also has the advantage that the bore may be extended through the full length of the cavity "C", even if the cavity is deviated from longitudinal.

Figures 19, 20:
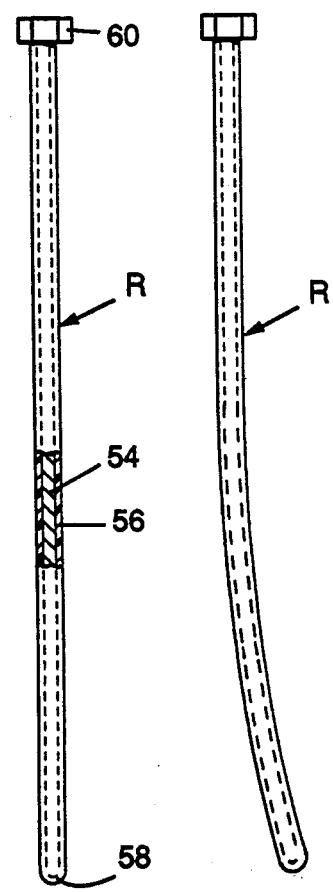
FIG. 19 is an elevational view of the smooth elongate rod used to form a bore in the fluid cement employed in the second embodiment; and, FIG. 20 is an elevational view of the rod shown in FIG. 19, illustrating how the rod may be bent to conform to the shape of the cavity within which the bore is being formed.

FIG. 19 shows the rod "R" in a straight condition, comprised of a malleable metal core 54 having a flexible sleeve 56 secured therearound. The sleeve is fabricated of a material having a low coefficient of friction, such as Teflon, and is formed so as to extend smoothly around the distal end 58 of the core 54. The proximal end of the core 54 is formed with a hexagonal head 60 to facilitate placement and removal of the rod "R".

FIG. 20 shows the rod "R" bent to a curvilinear configuration to correspond to the shape of a deviated cavity within which the rod is to be received. The rod may be preformed to this shape, or bent to this shape by the surgeon. Ideally the rod is sufficiently flexible so that, even if not truly of an arcuate curvilinear configuration, it may be easily removed from the bore within which it is received (as shown in FIG. 16).

Conclusion

While preferred embodiments of the invention have been illustrated and described, it should be understood that the invention is not so limited, but rather is defined by the accompanying claims. It is anticipated that the invention may find use in any environment where it is desired to remove a cement plug, or a portion of a cement plug, from a condition adhered to a bone. The invention is particularly well adapted to difficult removal situations, such as cement plugs adhered at the remote end of a cavity where the passage of the cavity has deviated alignment with respect to the plug.

We claim:

1. A method for removing a mantle of cement having an elongate curvilinear cavity formed therein from adhered condition with a bone recess, said method comprising:
    (a) filling the curvilinear cavity with fluid cement;
    (b) inserting an elongate curvilinear rod in the fluid cement;
    (c) permitting the cement to cure and form a unitary mass with the mantle;
    (d) withdrawing the curvilinear rod from the mass to form an elongate curvilinear bore therein;
    (e) tapping the bore to form a screw-threaded section therein;
    (f) engaging the screw-threaded section of the bore with a pulling tool; and,
    (g) imparting pulling force to the pulling tool to remove that portion of the mass within which the tool is threadably engaged from the recess.

2. A kit for removing a mantle of cement having an elongate cavity formed therein from adhered condition within a bone recess, said kit comprising:
    (a) a volume of fluid cement sufficient to substantially fill the curvilinear cavity, said cement being injectable into the curvilinear cavity and capable of curing to form an integral mass with the mantle;
    (b) a curvilinear rod insertable into the cavity to form a curvilinear bore in a volume of fluid cement injected into the curvilinear cavity;
    (c) a tap proportioned to form screw threads in a bore formed by the rod; and,
    (d) measuring means adapted for operative association with the tap to enable penetration of the tap into a bore to be limited.

* * * * *